(12) United States Patent
Peters

(10) Patent No.: US 8,348,370 B2
(45) Date of Patent: Jan. 8, 2013

(54) ASSAY SYSTEM AND METHOD

(75) Inventor: Kevin F. Peters, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 163 days.

(21) Appl. No.: 12/747,013

(22) PCT Filed: Jan. 18, 2008

(86) PCT No.: PCT/US2008/051495
§ 371 (c)(1),
(2), (4) Date: Jun. 9, 2010

(87) PCT Pub. No.: WO2009/091410
PCT Pub. Date: Jul. 23, 2009

(65) Prior Publication Data
US 2010/0261611 A1    Oct. 14, 2010

(51) Int. Cl.
*B41J 29/38* (2006.01)
*B41J 2/145* (2006.01)
*B41J 2/04* (2006.01)

(52) U.S. Cl. ............................. 347/12; 347/40; 347/54
(58) Field of Classification Search .................. None
See application file for complete search history.

(56) References Cited

U.S. PATENT DOCUMENTS

| | | | | |
|---|---|---|---|---|
| 5,467,115 | A * | 11/1995 | Childers | 347/47 |
| 6,123,410 | A * | 9/2000 | Beerling et al. | 347/42 |
| 6,309,828 | B1 | 10/2001 | Schleifer et al. | |
| 7,128,398 | B2 * | 10/2006 | DaQuino et al. | 347/49 |
| 7,163,284 | B2 | 1/2007 | Su et al. | |

* cited by examiner

*Primary Examiner* — Amber D Steele
*Assistant Examiner* — Lianko Garyu

(57) ABSTRACT

An array of electro-actuated fluid dispensers (200, 465, 500, 670) for metering out liquid reagents includes a support member (230); and a plurality of discrete electro-actuated fluid-dispensing die (220, 460) disposed on the support member (230), each of the die (220, 460) being configured to receive a supply of fluid (130, 300, 447, 454, 456, 665) being deposited thereon and dispense the fluid (130, 300, 447, 454, 456, 665) as needed for assay testing.

18 Claims, 7 Drawing Sheets

ASSAY SYSTEM AND METHOD

BACKGROUND

Conducting chemical reactions and using chemical reactions with a further measurement step in an assay is a practice widely used in biological, pharmaceutical, and chemical research as well as in vitro diagnostics. Billions of reactions and assays are performed annually. In a chemical reaction, two or more fluidic components are reacted to produce at least a third component. A fluidic component may be a reagent, such as a sample or a chemical. In an assay test, a chemical reaction among two or more fluidic components is used to determine any resulting activity, such as a concentration. Modern biological and pharmaceutical research frequently includes numerous assays for specific biological activities in cells or isolated biochemicals in order to discover novel biological targets for disease, new medicines directed to those targets, biological indications of a diseased or healthy condition, or other chemicals valuable in the agrochemical, foodstuffs, cosmetics, and other industries.

In drug discovery, for example, a sizeable number of assays (up to 1.5 million experiments per day in a single laboratory, for example) are prepared by combining two or more components. The assays may each contain a sample of a distinctive, unique chemical compound. These samples are tested to determine if any of the compounds they contain exert an effect or particular biological activity. Promising compounds are identified for further pursuit as potential therapeutic agents.

The fluidic components of the assay sample can be very expensive, unique, dangerous and/or in very limited supply. For efficiency and higher throughput, substantial attention has been devoted to reducing the sample volume of assays while advancing the ability of assays to discriminate small changes in biological activity. The combination and manipulation of these fluidic components rely on extreme accuracy and precision in dispensing small volumes of these fluids into reaction wells.

BRIEF DESCRIPTION OF THE DRAWINGS

The accompanying drawings illustrate various embodiments of the principles described herein and are a part of the specification. The illustrated embodiments are merely examples and do not limit the scope of the claims.

Throughout the drawings, identical reference numbers designate similar, but not necessarily identical, elements.

DETAILED DESCRIPTION

Figure 1A:
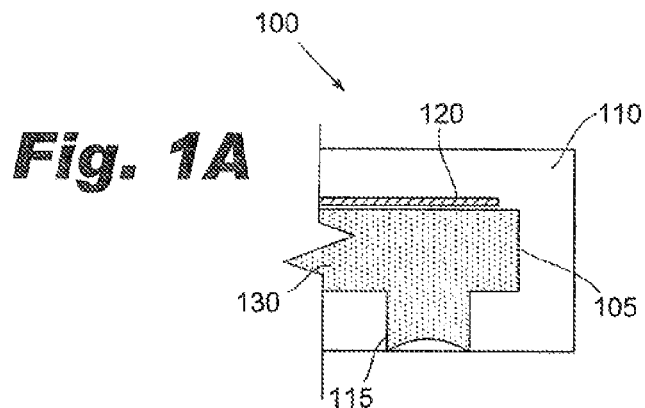
FIGS. 1A, 1B, and 1C are illustrative diagrams showing the operating principles of a thermal fluid-dispensing droplet generator, according to principles described herein.

A system that uses electro-actuated fluid dispensers for metering out liquid reagents is well suited to high throughput drug screening or other chemical reaction and testing or assay applications. By way of example and not limitation, the electro-actuated fluid dispensers may be a thermal inkjet die, a piezo-electric inkjet die, a piezo-electric capillary inkjet die, or a drop-on-demand device. For purposes of illustration, an assay method and system are described which use a thermal inkjet die as an electro-actuated fluid dispenser. Those of ordinary skill in the art will readily appreciate that the principles described herein are also applicable to reactions, simple dilutions, dispensing microliter, nanoliter, and picoliter volumes, by way of non-limiting examples.

Similar to other electro-actuated fluid dispensers, thermal inkjet dies are configured to precisely and repeatably dispense liquid reagents in assay applications. For example, a thermal inkjet die can dispense nanoliter volumes of fluids at frequencies as high as 50,000 droplets per second from each droplet generator. The system described below includes an automation and control system that uses inkjet-based or other fluid dispenser consumables. In these consumables, the fluid dispensing die are arranged in an array format, for example, as long reels of die disposed on a membrane, for example, a flexible membrane. This linear array of dies is configured to be spooled out, fluidically loaded, electrically tested, electrically actuated to perform one or many dispensing operations, and directed toward a take-up reel or other disposal system.

To perform these integrated functions, the system also automates source well plates for the loading of a fluid and automates destination well plates which receive the fluid dispensed by the fluid-dispensing dies into wells at prescribed volumes or doses. To perform this transfer of fluid from source to destination, the system provides separately for the loading of fluid from the source well plate to the dispenser and for the subsequent dispensing of fluid by the dispenser consumables to the destination. This loading may be automated via a dedicated device (e.g., a washable steel pin or syringe), or the loading may use a low-cost consumable such as reel-to-reel micro-pipettes (e.g., 'Mosquito'™ available at ttplabtech.com). The automation is integrated and controlled via user-directed control software that coordinates the various subsystems. This system addresses specific needs for high-throughput experimentation in drug discovery and is applicable to areas of bio discovery and industrial printing of substances other than drug candidates.

In the following description, for purposes of explanation, numerous specific details are set forth in order to provide a thorough understanding of the present systems and methods. It will be apparent, however, to one skilled in the art that the present apparatus, systems and methods may be practiced without these specific details. Reference in the specification to "an embodiment," "an example" or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

Figure 1B:
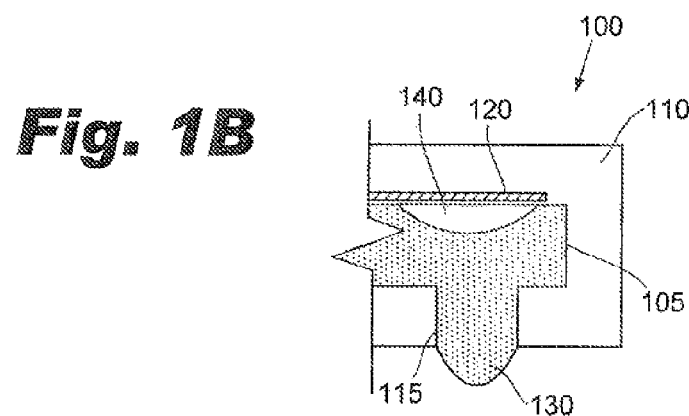
Figure 1C:
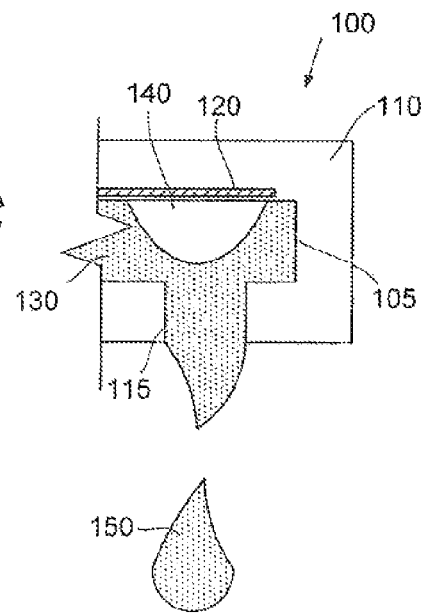

FIGS. 1A, 1B, and 1C are illustrative diagrams showing the operating principles of a thermal fluid-dispensing die. As will be appreciated by those skilled in the art, FIGS. 1A-1C are conceptual and do not necessarily attempt to illustrate the actual geometry of any particular fluid dispenser.

The fluid-dispensing die may contain one or more droplet generators (100). FIG. 1A a shows a cross-sectional diagram of a droplet generator (100) comprising a housing (110) which surrounds a firing chamber (105). An orifice (115) passes through the wall of the firing chamber (105). Fluid (130) enters the firing chamber (105) from a reservoir and fills the firing chamber (105) and interior of the orifice (115). A heating element (120) is proximally located to the firing chamber (105). The fluid (130) is contained within the firing chamber (105) such that the fluid does not exit the orifice (115) under iso-static conditions.

FIG. 1B shows the beginning of an ejection cycle in which electricity is passed through the heating element (120). The temperature of the heating element (120) rapidly rises and vaporizes a small portion of the liquid adjacent to the heating element (120). This vaporized fluid forms a vapor bubble (140) which rapidly expands and begins to force the fluid (130) below the bubble (140) out of the orifice (115). FIG. 1C shows the ejection of a droplet (150) from the orifice (115). The droplet (150) is ejected as a result of the vapor bubble (140) continuing to rapidly expand such that the surface and capillary forces which restrain the fluid (130) are overcome, thereby ejecting a droplet (150) from the droplet generator (100).

Following the rapid rise in temperature of the heating element (120) that causes the ejection of the droplet (150) the electrical current through the heating element (120) is discontinued and the heating element (120) rapidly cools. The vapor bubble (140) collapses, pulling additional fluid from the reservoir into the firing chamber (105) to replace the fluid volume vacated by the droplet (150). Additionally, capillary forces tend to draw fluid (130) into the firing chamber (105). When the channel (105) is again full of fluid, the droplet generator (100) is ready to begin a new droplet ejection cycle.

A plurality of droplet generators (100) may be contained within a single die. The die may be assembled for use individually or in an array. As mentioned above, a thermal inkjet is only one example of an electro-actuated fluid dispenser that can be configured to meter out liquid reagents. Other types of electro-actuated fluid dispensers such as piezo-electric inkjet die, a piezo-electric capillary inkjet dispenser, or a drop-on-demand device may be configured to dispense chemical or biofluids within an assay system.

The term "array", as used in the specification and appended claims, refers to an orderly series, arrangement, or sequence of a plurality of individual dispensing elements with a common support structure. The support structure may be solid, a membrane, and/or flexible. The array may contain a variety of spacing between elements and may be occasionally interrupted by a nonfunctional or missing element. In general, the array may extend in multiple physical dimensions. By way of example, a one dimensional array could refer to a row or column of elements, while a two dimensional array could refer to matrix having both rows and columns. The geometry and arrangement of the individual elements within the array can be altered such that the array is better adapted to accomplish a specific or general fluid-dispensing task. By way of example and not limitation, an array could be optimized for maximum element density within a given space or to match the spacing of a series of receptacles into which fluid will be dispensed.

Figure 2:
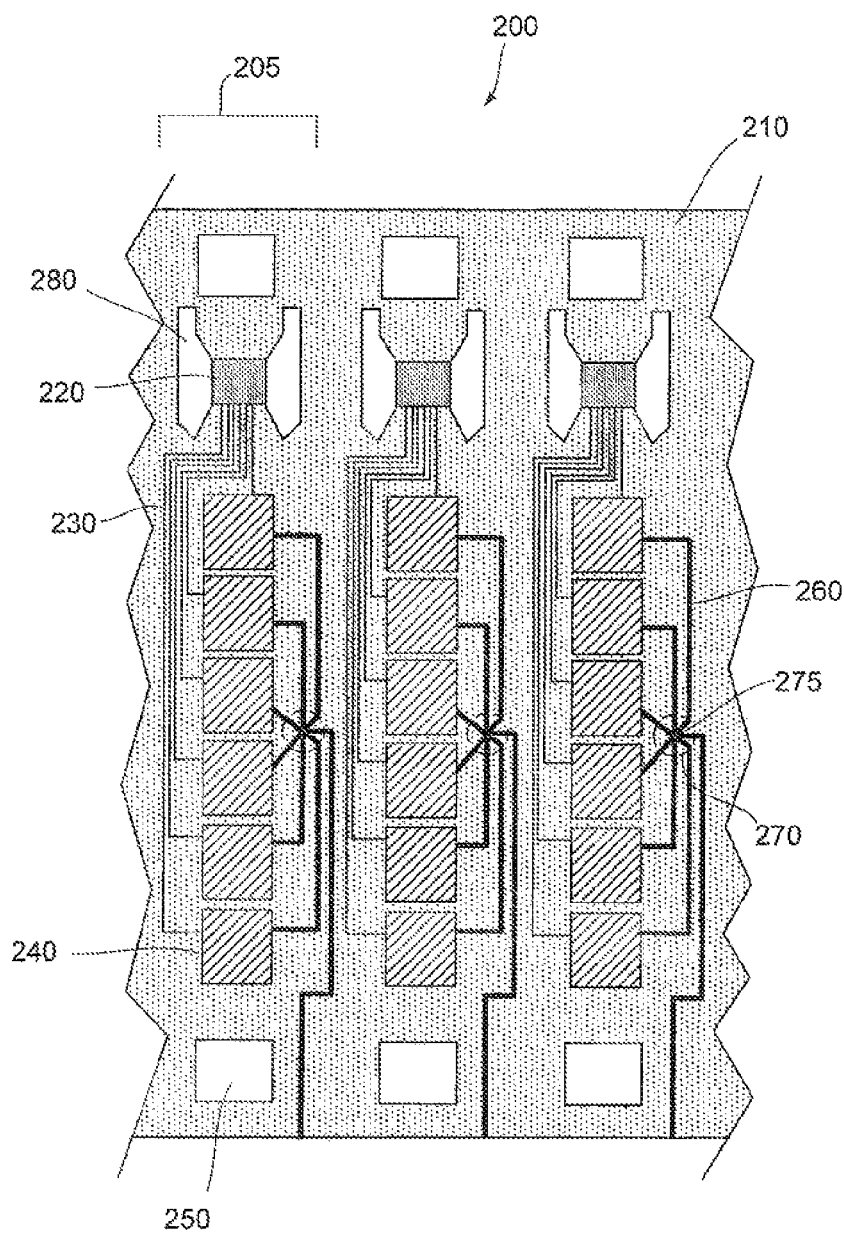
FIG. 2 is an illustrative diagram of an exemplary system for mounting fluid-dispensing die in a linear array format, according to principles described herein.

FIG. 2 is an illustrative diagram of an exemplary system for mounting a series of fluid-dispensing die in a linear array format. FIG. 2 shows a linear fluid-dispensing array (200) disposed on a carrier ribbon (210). Each functional unit in the array (200) is called a tab head assembly (205). Each tab head assembly (205) comprises a fluid-dispensing die (220) and the portion of the carrier ribbon (210) to which the die (220) is attached. In at least some embodiments, the carrier ribbon (210) may also comprise supporting traces (230) and electrical contact pads (240). The plurality of tab head assemblies (205) may be arranged in a linear array (200) or in any other suitable configuration including a two dimensional array. By way of example and not limitation, a two dimensional array may be configured in a sawtooth configuration, mirrored configuration with the inkjet die at the edges, or a mirror configuration with fluid-dispensing die (220) at the center.

The carrier ribbon (210) may be comprised of a variety of materials including polymer or composite materials, such as Kapton™ based substrates. The fluid-dispensing die (220) is mounted on the carrier ribbon (210) over exposed areas of traces (230). The fluid-dispensing die (220) may be held in place on the carrier ribbon (210) by a plurality of methods including adhesive, solder bonding, and wire bonding. The traces (230) make an electrical connection between the internal electrical components of the fluid-dispensing die (220) and the contact pads (240). The contact pads (240) allow an external electrical connection to be made that provides access to, and control of, the internal functions of the fluid-dispensing die (220).

In one illustrative embodiment, the carrier ribbon (210) has a plurality of through-holes (280) disposed on either side of the fluid-dispensing die (220). Additionally, the carrier ribbon (210) may have other through-holes such as rectangular traction holes (250) on the top and bottom edges of the carrier ribbon (210). The traction holes (250) allow automation machinery (not shown) to grip the carrier ribbon (210) and move it precisely through various processes such as assembly, use, and disposal of the linear fluid-dispensing array (200). Additionally, the carrier ribbon (210) or other support member may have a variety of holes, fiducial marks, capacitive features, optical features, or other elements which provide for more precise alignment and positioning of the array of electro-actuated fluid dispensers.

The carrier ribbon can be configured to hold a plurality of tab head assemblies (205) at very closely spaced intervals. By way of example and not limitation, the linear fluid-dispenser array (200) may be comprised of tab head assemblies (205) with center-to-center spacing of 9 mm, 4.5 mm, or 2.25 mm. According to one illustrative embodiment, the electro-actuated fluid dispensers are regularly spaced at intervals that correspond to the spacing of the wells in a standard well plate. In two dimensional arrays, the electro-actuated fluid dispensers may be similarly spaced at in a second direction. Due to manufacturing yield, there may be an absent, inactive, or inoperable electro-actuated die within the array which disrupts the regular spacing of operable die. Absent, inactive or defective die can be identified and the operation of the system can be modified as described below with respect to FIG. 4.

According to one illustrative embodiment, the deposition of the contact pads (240) and traces (230) is accomplished by electroplating selected areas of the carrier ribbon (210). The electroplating process uses electrical current to coat electrically conductive portions of the carrier ribbon (210) with a relatively thin and flexible layer of metal. The electroplating process increases the thickness of the conductive portions of the carrier ribbon as well as improving other properties of the traces (230) and pads (240). In one illustrative embodiment, an anode is made of metal to be coated onto the carrier ribbon (210) and portions of the carrier ribbon are charged to form the cathode of the circuit. The components are immersed into an electrolyte solution containing metal ions. As electrical current flows through the circuit, the metal ions plate the cathode regions on the carrier ribbon (210). The anode slowly dissolves to replenish the metal ions in the electrolyte solution.

To facilitate the electroplating process, all of the areas within the carrier ribbon (210) that are to be plated are electrically connected to a single point (275) by manufacturing traces (260). It should be noted that the manufacturing traces (260) are separate from the traces (230) described above that are used to control a fluid-dispensing die (220) when manufacturing is complete. One of the manufacturing traces (260) connects the connection point (275) to the edge of the carrier ribbon (210). The desired electrical contact for electroplating can then be made to all the areas where plating is needed by making a single electrical connection along one edge of the carrier ribbon (210) to the manufacturing trace that extends to the ribbon edge.

After the electroplating is complete, the electrical connections formed by the manufacturing traces (260) are severed prior to the use of the linear inkjet array (210). By way of example and not limitation, this is accomplished by punching out the connection point (275) as indicated by the dashed circle (270), which breaks the electrical connection among the pads (240) formed by the manufacturing traces (260).

Figure 3:
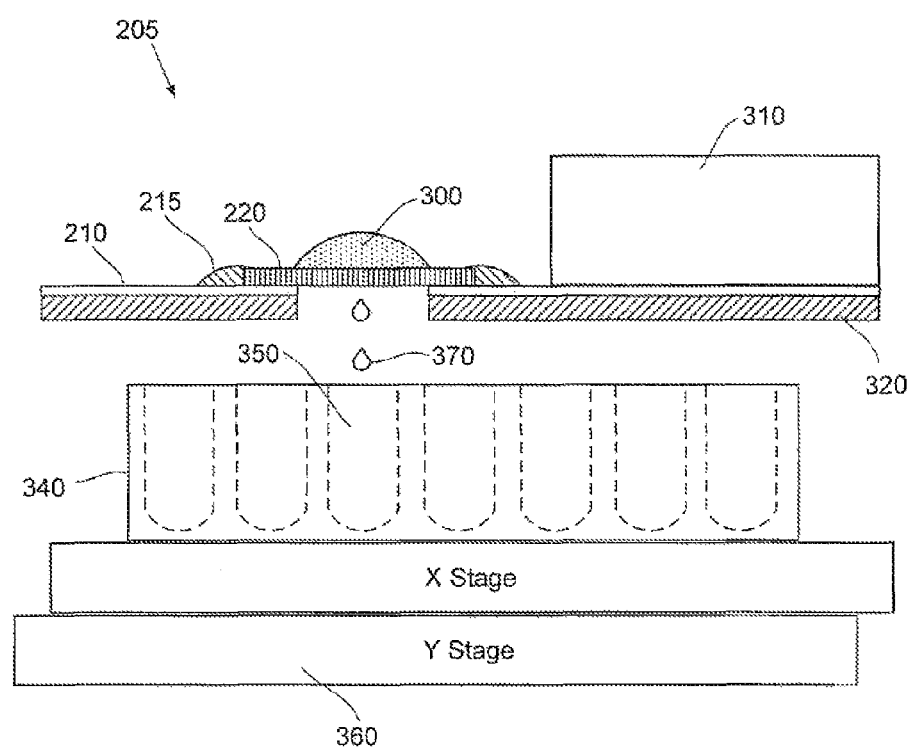
FIG. 3 is an illustrative diagram of an exemplary system for dispensing chemicals or biofluids using a fluid-dispensing array, according to principles described herein.

FIG. 3 is an illustrative diagram of one exemplary system for dispensing chemicals or bio-fluids using a fluid-dispensing tab head assembly (205), according to principles described herein. As discussed with reference to FIG. 2, the tab head assembly (205) comprises a fluid-dispensing die (220), a portion of the support membrane, its associated electrical traces (230, FIG. 2) and contact pads (240, FIG. 2). According to one illustrative embodiment, the fluid-dispensing die (220) may be attached to the carrier ribbon (210) by adhesive joints (215). The fluid-dispensing die (220) can be configured to receive a quantity of fluid (300) on the upper portion of the fluid-dispensing die (220). According to one illustrative embodiment, the fluid may comprise a potentially therapeutic component in combination with dimethyl sulfoxide (DMSO), water, and/or another solvent. Also, as described above, the tab head assembly (205) may be one portion of an array of tab head assemblies.

The method of electrically actuating, the fluid dispensers may comprise a computer or other control means to make electrical contact through traces to the fluid dispensers. According to one illustrative embodiment, a contact head (310) makes electrical connections with the contact pads (240, FIG. 2) by pressing down on the carrier ribbon (210). The resulting electrical connections allow a controller or computerized device to control the operation and functionality of the fluid-dispensing die (220). This electrical contact may be maintained throughout the active operations of the electro-actuated fluid dispenser or may be reestablished at the various stations or during operations. Electrical contact may be made simultaneously to a plurality of electro-actuated fluid dispensers. Following electrical contact by contact head (310) to a fluid dispenser, a subsequent electrical contact to a second fluid dispenser may be made.

The carrier ribbon (210) can be supported by a support element (320) to provide accurate positioning and more robust operation. In one illustrative embodiment, the support element (320) has an aperture through which the fluid-dispensing die (220) can eject droplets (370) onto a target. One target may be an assay plate (340) that is comprised of a two-dimensional array of assay wells (350). The assay plate (340) can be mechanically positioned or actuated by a variety of mechanisms including an X/Y stage (360). The X/Y stage (360) provides for precise motion of the assay plate (340) in an X direction and Y direction. This allows the assay plate (340) to be positioned under the fluid-dispensing die (220) such that the droplets (370) are precisely and accurately delivered into specific individual wells (350) and or specific positions within specific wells. The assay plate (340) may also be mechanically positioned or actuated in a Z direction such that the vertical positioning of the assay plate (340) can be adjusted.

Figure 4:
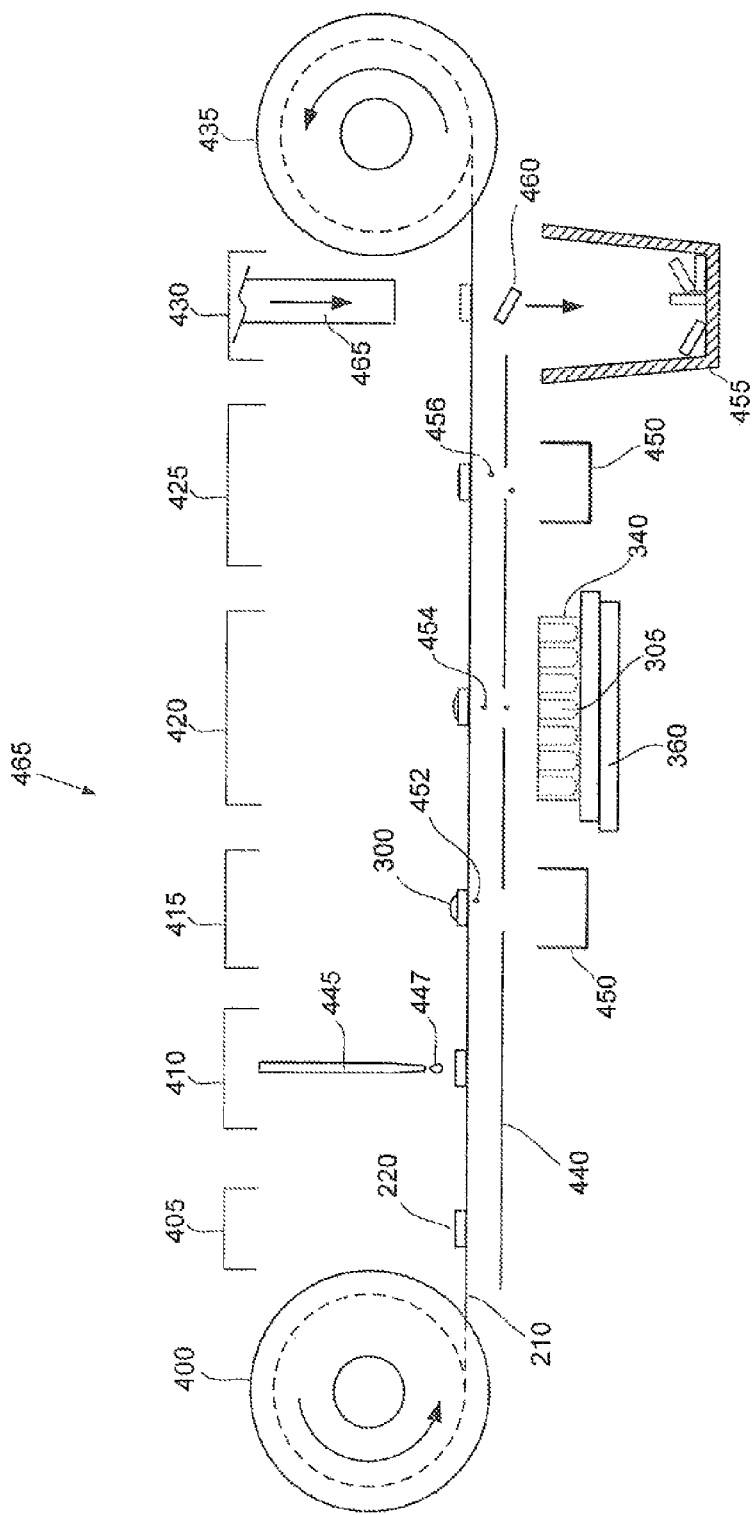
FIG. 4 is an illustrative diagram of an exemplary system configured to dispense chemical or biological fluids using a roll-to-roll linear array of fluid-dispensing die, according to principles described herein.

FIG. 4 is an illustrative diagram of an exemplary system (465) for dispensing chemical or biological fluids using a roll-to-roll linear fluid-dispensing array (200). The linear fluid-dispensing array (200) is initially spooled on a dispensing reel (400). As discussed above, the linear fluid-dispensing array (200) may comprise any given number of tab head assemblies (205) disposed on a flexible ribbon (210). The linear fluid-dispensing array (200) is progressively unrolled from the dispensing reel (400) and passes through a variety of stations (405, 410, 415, 420, 425, 430) and then is rolled onto a take-up reel (435). The carrier ribbon (210) is repositioned so as to provide functional operation of a succession of inkjet die through the stations. Each of the stations (405, 410, 415, 420, 425, 430) will now be described in sequential order.

According to one illustrative embodiment, a removable protective layer, such as sterile tape, could be disposed on the top of the tab head assemblies to prevent contamination prior to use. The removable protective layer, if used, may be removed as the array is unreeled from the dispensing reel (400). In some embodiments, the removable protective layer may be wound onto a separate spool.

A first station may consist of a dry test station (405). At the dry test station (405), the presence of the die may be tested. In another embodiment, the tab head assembly (205) can be electrically connected to test equipment to ensure the electrical viability of a variety of elements within the tab head assembly (205). By way of example and not limitation, these tests could include determining if the intersection (275, FIG. 2) of the, manufacturing traces (260, FIG. 2) had been correctly and accurately punched out. An additional test can include measuring the connection to and resistance of the heating elements (120, FIG. 1) within the fluid-dispensing die (220). Further, the dry test station (405) procedure may involve reading information which may be encoded with the die (220).

At each of the stations (405, 410, 415), functional characterization can be performed including detecting malfunctions in a given tab head assembly (205) and then taking appropriate corrective action. The corrective action may vary from station to station. For example, if the tab head assembly (205) does not correctly operate at the dry test station (405), that tab head assembly (205) can be electronically or otherwise identified as defective. As the defective tab head assembly progresses through the remaining stations, no further action would be taken to utilize the defective tab head assembly.

The next operation occurs at the loading station (410). At the s loading station, a loading mechanism (445) dispenses fluid (447) onto the upper surface of the fluid-dispensing die (220). By way of example and not limitation, the loading mechanism (445) may comprise a micropipette, a syringe, pin mechanism, or any other device that is suitable for placing fluid (447) on the upper surface of the die (220). During loading, a slight positive or negative pressure may be applied to the fluid. Loading the fluid (447) onto the upper surface of the fluid-dispensing die (220) can be performed either manually or automatically and may be continued during the course of other operations, including dispensing. Automatic mechanisms may include reel-to-reel micropipettes, reel-to-reel pin automation, pin array, or other automated pipetting means such as singulated disposable pipettes. For example, loading could be accomplished using any number of commercially available systems such as the Mosquito™ micropipette automation system from TTP Labtech. The amount of fluid dispensed by the loading mechanism (445) may vary according to the capacity of the die (220) to retain the fluid, the amount of fluid that is desired to be dispensed onto the target, or other factors.

The fluid carrying capacity of the die (220) may be increased using a slot extender or other fluid containing means. According to one illustrative embodiment, a slot extender is a plastic cup or other container that is attached to the upper surface of the die. The slot extender has an open top configured to receive the fluid from the loading mechanism (445). The bottom surface of the slot extender is configured to be in fluid contact with the die (220) such that fluid within the slot extender can be dispensed through the droplet generators (100, FIG. 1) of the fluid-dispensing die (220).

The next operation occurs at the wet test station (415). At the wet test station (415), the fluid (300) placed on the upper surface of the inkjet die (205) is dispensed by the die (205) as ejected droplets (452) into a fluid receptacle (450). The wet test station (410) can serve a variety of functions including a check of the operational ability of each of the droplet generators (100, FIG. 1) contained within the fluid-dispensing die (220). In addition to basic functionality, the size, speed, and accuracy of the injected droplets (452) may be measured. Characteristics of the loaded fluid, dispenser, and/or the s dispensing may be acquired from the computer memory, a look-up table, the dies itself, end user input, and/or from measure performance.

The wet test station (415) may also verify that the functions within the loading station (410) have been correctly performed. By way of example and not limitation, a temperature sensor within the fluid-dispensing die (220) could be used to detect a temperature change within the fluid-dispensing die (220) when a droplet of fluid is placed on its upper surface. For example, the fluid (300) and the fluid-dispensing die (220) may be at different temperatures. The fluid (300) may be chilled or the fluid-dispensing die (220) heated using resistive elements. The contact between the fluid (300) and fluid-dispensing die (220) would then result in a temperature change that could be detectable by the temperature sensor in the fluid-dispensing die (220). This would confirm that the loading process had occurred.

Additionally, a variety of sensors could be utilized within the system to provide superior levels of performance and certainty by monitoring, calibrating, correcting or reporting. By way of example and not limitation, a loading monitor could be used to measure and verify the desired operation within the loading station. Similarly, a priming monitor could be used at the wet test station to determine if each droplet generator within the die is primed and ready to dispense fluids in the desired manner. Further, a dispensing monitor may be used to verify and characterize the dispensing of the specific fluid by a die.

At the dispense station (420), the tab head assembly dispenses fluid (454) as precisely metered and accurately delivered fluid droplets (454). The fluid droplets (454) could be received by assay plate (340) which may be positioned by an X/Y stage (360) or by other means relative to the tab head assembly (205). Consequently, the tab head assembly (205) may dispense one or many droplets (454) into a given well or wells (350) of the assay plate (340). Similarly, the electro-actuated fluid dispensers may deposit droplets onto a Petri dish, a chip, a prepared glass slide, a card, an absorbing surface, or other substrate.

A sensor or sensors may be used to confirm that the fluids are s dispensed as desired. By way of example and not limitation, a sensor could measure the droplets dispensed, the frequency of the droplets, the volume of fluid dispensed, the location of the droplets, or other parameters. Additionally, a sensor or sensors could measure characteristics of the dispensed fluid. By way of example and not limitation, the sensor could measure the specific fluid concentration of components within the fluid. These components may include DMSO, water, therapeutic agent, solvents, and/or other fluids. Measured parameters of the fluid, dispenser, or other functionality may be used in conjunction with a look up table to recalibrate the dispensing parameters. For example, the drop size, the number of drops needed, the heater pulse energetics and other parameters could be optimized to improve dispensing volume control.

Further, sensors could be incorporated into a closed loop system in which various parameters are monitored and corrective action is taken. In the event that corrective action is needed to correct a failure in at least one of the positioning, priming, dispensing, droplet ejection, or other operations, the system can take a coordinated and predetermined action to rectify the situation. For example, additional droplets could be dispensed to compensate for a failed droplet event or a too-small droplet volume. Alternatively, the sensors could trigger an alert or warning, stop the operation and wait for a technician to assess the situation or take other action.

At the post dispense station (425), each tab head assembly (205) can again be tested to determine the volume and quantity of the droplets delivered, the concentration of fluid components such as water or compound, or other operational characteristics of the droplet generators (100). Additionally, the post dispense station (425) could be utilized to recover precious or expensive fluids from the inkjet head. A receptacle (450) can be positioned beneath the tab head assembly (205) to receive any remaining fluid (456) stored on or in the tab head assembly (205).

The disposal station (430) may comprise a mechanical stamp (465) that punches out the used inkjet die (205) into a waste receptacle (455). The punched out inkjet die (460) are received into the waste receptacle (455) for appropriate disposal and recycling. Appropriate disposal of the used inkjet die can be important to prevent contamination or exposure to the chemical solutions dispensed by the inkjet die (205).

According to one illustrative embodiment, the remaining chemicals within the inkjet die are eliminated prior to disposal. One method of eliminating the remaining chemicals includes thermal annihilation of any remaining chemicals within the fluid-dispensing die (220) by the prolonged activation of the heating elements (120) and/or other resistive heaters contained within the fluid-dispensing die (220). Another possibility includes washing or is flushing out the biological or chemical fluid (300) such that the fluid-dispensing die (220) can then be disposed, recycled or reused. By way of example and not limitation, the solvent dimethyl sulfoxide (DMSO) could be used to flush out the fluid-dispensing die (220).

In yet another disposal embodiment, the tab head assemblies (205) could be sealed, reeled up onto the take-up reel (435) and then disposed of appropriately. One method of sealing the tab head assemblies (205) prior to reeling them up on the take-up reel (435) might include covering the fluid-dispensing die (220) with a protective cover such as plastic or aluminum tape. An alternative method could include sealing the reel within a cassette box.

A shield plate (440) may be used to passively or actively prevent contamination of fluid, dispensers, loaders, well plates, and subsystems. The shield (440) may take a variety of configurations and is shown here as a plate with a number of apertures. By way of example and not limitation, the shield plate may comprise a number of guards, doors, walls or other features that isolate the various stations and prevent external or cross contamination. The shield plate (440) may also have a support function, similar to the support plate (320, FIG. 3) illustrated in FIG. 3. A shield enclosure, not shown, may be used to shield portions or the entirety of the system. Such an enclosure may be used to control the level, admission, or emission of any of: humidity, airborne contaminants, particles, micro-organisms, light, air flow, aerosols, vapors, body parts, and/or other safety or environment factors.

The order and location of operational stations (405 through 430) can be altered according to usage and efficiency needs. By way of example and not limitation, a single operational station could combine the functions of a plurality of stations described above. For example, the fluid-dispensing die (220) could be tested, loaded, and dispense the fluid at a single station. A single electrical contact mechanism (310) could be used to perform all the testing and dispensing operations. Additionally, several different loading operations could be performed prior to dispensing. Then, the several dispensing operations could be performed serially or in parallel. For example, the loading may be from several "hit" locations or wells within a source well plate.

Many of the functions within each operational station (405 through 430) could also be performed in parallel. For example, several loading operations can be performed in parallel, thereby loading fluid simultaneously onto a plurality of inkjet dies (220). By way of example and not limitation, the droplet generators (100) of each fluid-dispensing die (220) could have spacing that is substantially the same as the well spacing on an assay plate (340). For example, the tab head assemblies (205) may be arranged with a center-to-center spacing of 9 mm, 4.5 mm, or 2.25 mm, thereby matching the well spacing of several types of standard assay plates. According to another illustrative embodiment, a plurality of tab head assemblies (205, FIG. 3) are loaded and utilized to simultaneously dispense liquid into a row of wells (305) in the assay plate (340). In another embodiment, loading and dispensing may proceed in parallel by initiating dispensing before loading is complete, there by using the loading device as an enhanced-volume reservoir for the dispenser.

The carrier ribbon (210) utilized within the roll-to-roll dispensing system (465) could have a large number of tab head assemblies per reel. By way of example and not limitation, 100 to 10,000 such tab head assemblies could be on each reel. Alternatively, the number of tab head assemblies in an array could be arranged to match the well configurations of a standard assay plate, with lengths as short as 8, 96, 384, or 1536 tab head assemblies. According to one illustrative embodiment, the tab head assemblies are s arranged in a two dimensional array that matches the well spacing in an assay plate. In this embodiment, the tab head array could simultaneously dispense liquid into all or part of the wells contained within the assay plate.

The roll-to-roll system described above is only one example of a system that utilizes electro-actuated fluid dispensers arranged in an array format. By way of example and not limitation, the system may comprise a dispensing reel which is unwound, utilized, and then disposed of without being wound onto a take-up roll.

Figure 5:
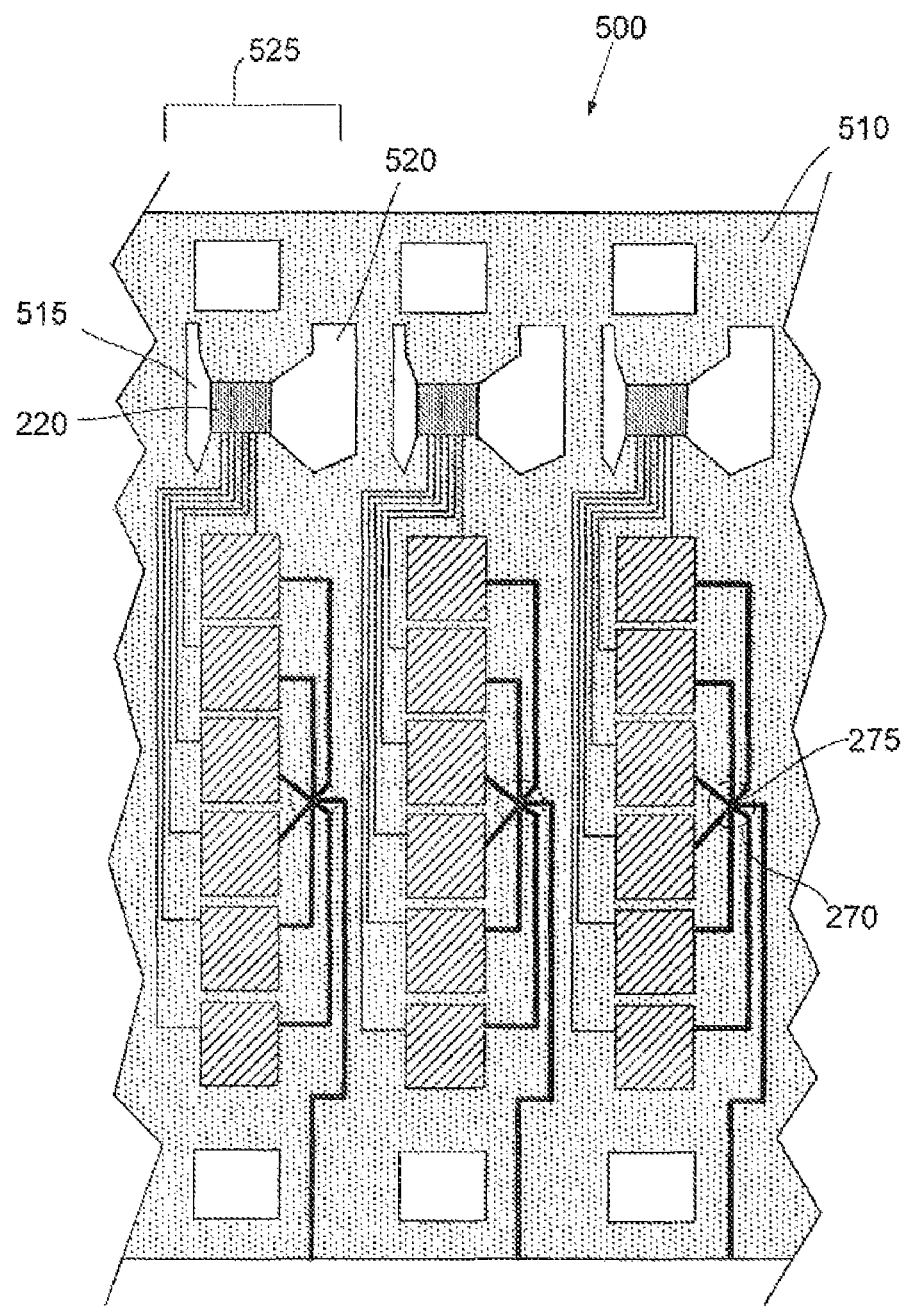
FIG. 5 is an illustrative diagram of an exemplary system for mounting a fluid-dispensing die in a linear array format, according to principles described herein.

FIG. 5 is an illustrative diagram of one exemplary design for creating a linear inkjet array (500). The linear inkjet array (500) allows for more convenient and rapid loading of fluid onto the fluid-dispensing die (220).

According to this illustrative embodiment, the carrier ribbon (510) is configured to receive the fluid-dispensing die (220) and its associated traces and pads as described in FIG. 2 and its corresponding text. The through-holes located on either side of the fluid-dispensing die (220) are altered. A first through-hole (515) is narrower than the previous through-hole (280, FIG. 2), while second through-hole (520) on the opposite side of the fluid-dispensing die (220) is enlarged. This enlarged through-hole (520) creates an access opening which allows a micropipette or other similar instrument to pass through the carrier ribbon (510) to access a source well plate or other container that is immediately below the carrier ribbon (510). The enlarged through hole may be utilized for other operations such as passing a stream of fluid or a beam of light, positioning, sensing or other function.

According to one illustrative embodiment, the micropipette is passed through the carrier ribbon (510) and brought into contact with the fluid contained in a source well plate below or behind the carrier ribbon (510). The micropipette then draws a portion of the fluid into its internal reservoir. The micropipette is then retracted through the enlarged through-hole (520) and is moved a short distance such that the micropipette is over the fluid-dispensing die (220). The micropipette then dispenses the desired amount of fluid on the upper surface of the fluid-dispensing die (220) from which the die (220) can dispense the fluid in a controlled manner.

Figure 6:
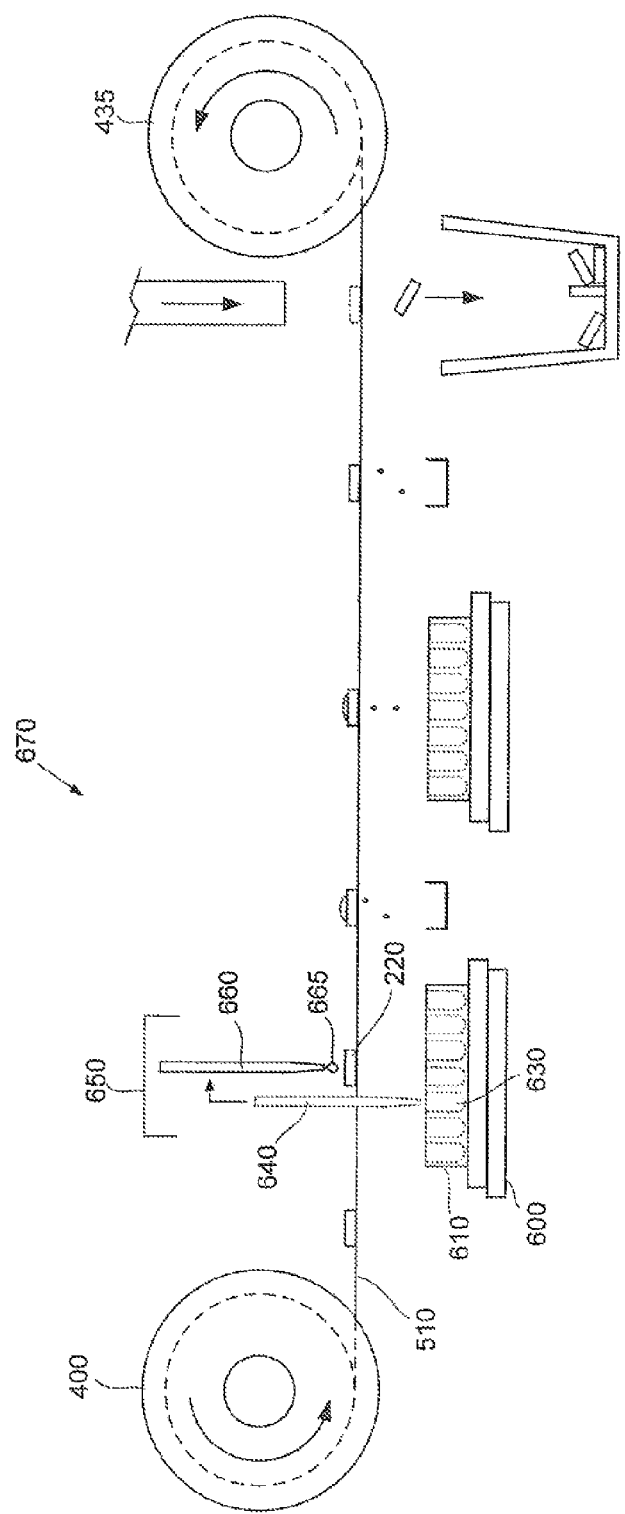
FIG. 6 is an illustrative diagram of an exemplary system for dispensing chemical or biological fluids using a roll-to-roll linear array of fluid-dispensing heads, according to principles described herein.

FIG. 6 is an illustrative diagram of an exemplary system (670) for dispensing chemical or biological fluids using a roll-to-roll linear array of inkjet die disposed on a carrier ribbon (510) with enlarged through-holes (520) as described above. In this illustrative embodiment, a carrier ribbon (510) is initially contained on the dispensing reel (400). The carrier ribbon (510) is unrolled and the tab head assemblies (525, FIG. 5) progress through stations similar to those described with reference to FIG. 4.

However, the operation of the loading station (650) makes use of the enlarged through-hole (520, FIG. 5) in the carrier ribbon (510). The enlarged through-hole (520, FIG. 5) allows a micropipette (660) or similar device to pass through the carrier ribbon (510) into a take up position (640). In the take up position (640), the micropipette (660) can access a source well (630) contained in an assay plate (610). An X/Y stage (600) may be used to position the desired source well (630) under the enlarged through-hole (520, FIG. 5). The automated pipette (660) can then be retracted to a dispensing position as illustrated in FIG. 6. The desired amount of fluid (665) can then be dispensed onto the upper surface of the fluid-dispensing die (220). By using the enlarged through-hole (520, FIG. 5) as an access point, the micropipette (660) need only move a minimal distance to deliver the fluid to the fluid-dispensing die (220). The loading process is thereby simplified and can be performed more rapidly. In situations where the loading process is a bottleneck, faster loading times can result in higher throughput and greater efficiency of the overall system.

Figure 7:
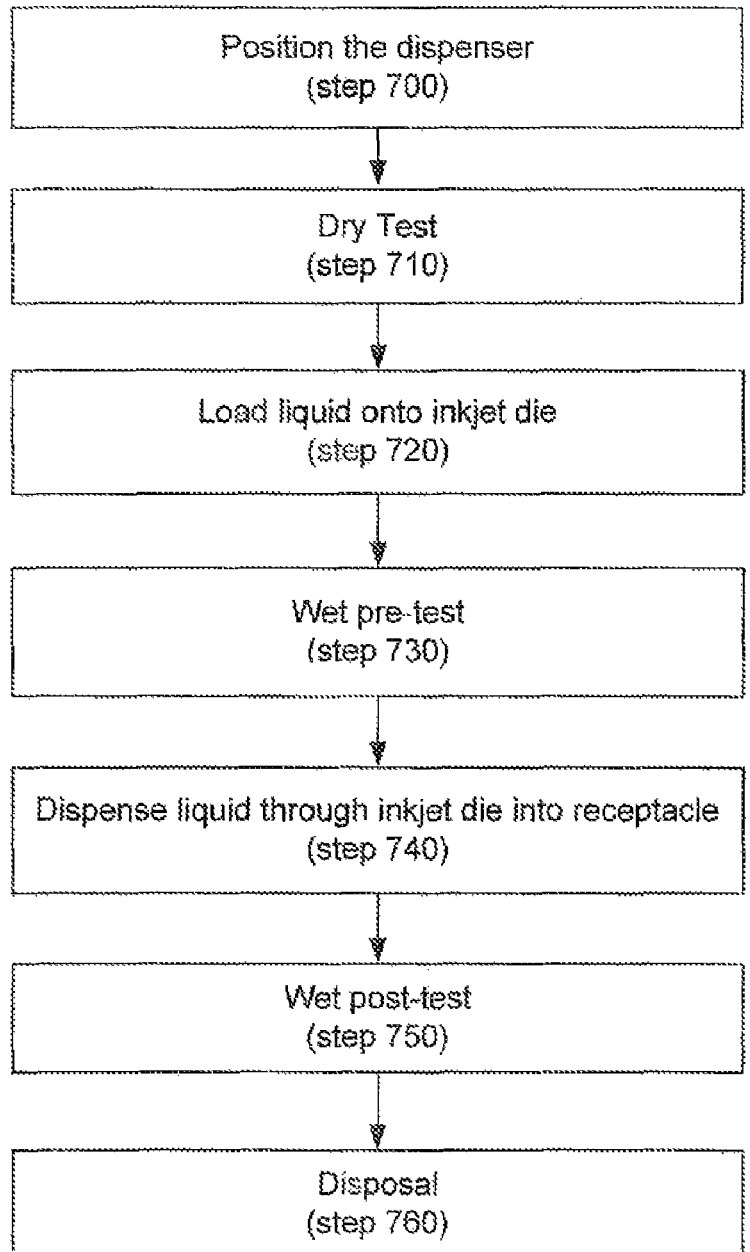
FIG. 7 is an illustrative flowchart showing an exemplary method of dispensing chemical or biological fluids using a roll-to-roll linear in jet array, according to principles described herein.

FIG. 7 is an illustrative flowchart showing one exemplary method of dispensing chemical or biological fluids using a fluid-dispensing array. The tab head assembly is first positioned to begin testing (step 700). According to one illustrative embodiment, the tab head assembly is positioned by unrolling it from a dispensing reel. The second step may be a dry test in which electrical or other tests could be performed to verify the functionality of the tab head assembly (step 710). The dry test could assess the tab head assembly to determine if its electrical characteristics are within an acceptable range or ranges.

Following successful completion of the dry test, liquid is loaded onto the inkjet die (step 720). In some embodiments, a wet pre-test is then performed to determine if the inkjet die performs correctly and dispenses the anticipated amount of fluid (step 730). The liquid is then dispensed from the inkjet die onto a target or other receptacle (step 740). In some embodiments, a wet post test (step 750) is also performed to confirm the continued operation of the inkjet chip. By way of example and not limitation, the wet post test could, verify the existence and size of the ejected droplets. The existence of droplets verifies that the fluid supply of the inkjet die was not entirely consumed during the dispensing process and that the droplet generators are still functioning. The size of these droplets allows for the verification of the amounts dispensed into is the assay well or other target. Additionally, expensive or unique fluids could be recovered during the wet post test.

Following the post test, disposal of the inkjet die and the remaining fluid within the inkjet die can be completed (step 760). In one illustrative embodiment, the remaining fluid within the inkjet die can be disabled as part of the disposal step using chemical, thermal, electrical, or mechanical means. To disable the fluid chemically, chlorine gas, chlorine solution, acid, base, ozone gas or other reactive chemicals may be used. The disposal of the fluid can be performed by a variety mechanical methods, including flushing out the fluid and washing the inkjet die. This allows the inkjet die within the array to be reused. Another means of disposing of the remaining fluid in the inkjet die is to thermally annihilate or autoclave any residual chemical or bio fluid that remains in the inkjet die. The inkjet die contains a number of resistive heating elements, including the elements (120, FIG. 1) used to operate the inkjet droplet generators (100, FIG. 1). These resistive elements can be used to raise the temperature of the inkjet die (220, FIG. 2) sufficiently that all biological or chemical residues are vaporized or otherwise neutralized. Another method of disabling the fluid is to seal the used inkjet dies, then roll the carrier ribbon and the tab head assemblies onto an outtake reel (435, FIG. 6). According to one illustrative embodiment, the used inkjet dies are covered with a membrane, such as an adhesive tape that seals the fluids inside the inkjet die. Following the optional step of disabling the fluids remaining within the inkjet die, the die s may then be disposed of by a variety of means including stamping the used inkjet die out of the carrier ribbon into a waste receptacle for recycling.

In sum, a fluid-dispensing array can be combined with other automation to create a highly effective system for manipulating, dispensing, and disposing of fluids in a high throughput assay environment. Inkjet technology is ideally suited for rapid, precise, and repeatable dispensing of assay components into reaction wells. This inkjet technology can be automated by creating tab head assemblies disposed on a flexible ribbon. These tab head assemblies can be stored, used, and disposed of on a reel-to-reel system that greatly simplifies the work flow and adds value. The inkjet die can outperform existing systems in terms of throughput and in terms of volumetric precision, particularly in the sub-microliter, nanoliter, and picoliter ranges. The inkjet technology enables the miniaturization of drug-screening assays and other experimental types where the samples or the reactive chemicals are unique, precious or very expensive. Additionally, multiple dispense operations can be performed in a non-contact fashion from a single inkjet device. The inkjet die are cost-effective and disposable, but may in certain cases be robust enough to be reused multiple times.

The preceding description has been presented only to illustrate and describe embodiments and examples of the principles described. This description is not intended to be exhaustive or to limit these principles to any precise form disclosed. Many modifications and variations are possible in light of the above teaching. Other common elements of standard reel and reel-to-reel technology that have not been described here are nonetheless understood to be applicable. A nonexclusive list of such reel technology may include leader tape, splicing, and others.

What is claimed is:

1. An array of electro-actuated fluid dispensers for metering out liquid reagents comprising:
    a support member; and
    a plurality of discrete electro-actuated fluid-dispensing die disposed on said support member, each of said die comprising an open cup disposed on an upper surface thereof, said cup being configured to receive a supply of fluid being deposited therein, said cup also being in fluid communication with an interior of said fluid-dispensing die such that fluid deposited in said cup is fed into said fluid-dispensing die which will dispense said fluid as needed for assay testing.

2. The array of claim 1, wherein said support member is a flexible ribbon configured to be wound onto a dispensing reel.

3. The array of claim 1, wherein said support member is a flexible ribbon partially wound on a dispensing reel and partially wound on a take-up reel such that said plurality of dispenser die can be moved from said dispensing reel to said take-up reel.

4. The array of claim 3, wherein said support member comprises regular fraction holes for driving said support member between said reels.

5. The array of claim 1, wherein said support member further comprises alignment features.

6. The array of claim 1, wherein said die are individually addressable by electrical contacts disposed on said support member, wherein said electrical contacts are connected to said die by a plurality of traces disposed on said support member.

7. The array of claim 6, further comprising manufacturing traces disposed on said support member wherein said manufacturing traces connect with each of said electrical contacts so as to support electroplating to form said electrical contacts.

8. The array of claim 7, wherein said manufacturing traces join at a single point that is also electrically connected through a manufacturing trace to a manufacturing contact disposed on said support member.

9. The array of claim 7, wherein said electrical contacts are electrically disconnected from each other by severing said manufacturing traces.

10. The array of claim 1, wherein said plurality of discrete die are in an array with spacing corresponding to a standard assay well spacing.

11. The array of claim 1, further comprising a through-hole in said support member adjacent each of said die, said through-hole accommodating a fluid transport device extending through said support member for loading from a supply below said support member such that said fluid transport device then retracts and supplies fluid to a said die.

12. The array of claim 1, wherein said discrete die disposed on said support member are covered by a separator membrane, said separator membrane being removed prior to said die receiving said fluid.

13. A method for conducting assay testing by delivering fluid through the use of a fluid-dispensing die, said method comprising:
 loading said fluid onto a fluid-dispensing die, said die being one of a plurality of die contained within an array, said die comprising an open cup disposed on an upper surface of said die, the cup being in fluid communication with a reservoir and a droplet generator, said droplet generator configured to dispense said fluid received through said cup into said reservoir; and
 selectively actuating said die to dispense a quantity of said fluid through said droplet generator to a substrate surface.

14. The method of claim 13, wherein said die are arranged in a linear array on a flexible ribbon, said method further comprising moving said ribbon from a dispensing reel to a take-up reel.

15. The array of claim 1, wherein the support member comprises an aperture over which a fluid-dispensing die is disposed such that said fluid-dispending die is arranged to dispense fluid through said aperture in said support member.

16. The array of claim 1, further comprising a protective tape disposed over said cups of said fluid dispensing die, said protective tape being removable prior to loading of fluid in said cups.

17. The array of claim 1, further comprising a temperature sensor incorporated with each fluid-dispensing die, said temperature sensor configured to sense a change in temperature that occurs when fluid is loaded in said cup and to signal that loading of said cup with fluid has occurred.

18. A method of using the array of electro-actuated fluid dispensers for metering out liquid reagents of claim 1, said method comprising:
 with a separate liquid dispensing device, dispensing said fluid into said open cups of said fluid dispensing dies to load said dies with fluid; and
 with said fluid dispensing dies, dispensing said fluid into an assay plate for assay testing.

\* \* \* \* \*

UNITED STATES PATENT AND TRADEMARK OFFICE
CERTIFICATE OF CORRECTION

PATENT NO. : 8,348,370 B2
APPLICATION NO. : 12/747013
DATED : January 8, 2013
INVENTOR(S) : Kevin F. Peters Page 1 of 1

It is certified that error appears in the above-identified patent and that said Letters Patent is hereby corrected as shown below:

In column 12, line 39, in Claim 4, delete "fraction" and insert -- traction --, therefor.

Signed and Sealed this
Second Day of April, 2013

Teresa Stanek Rea
*Acting Director of the United States Patent and Trademark Office*